(12) United States Patent
Yoo et al.

(10) Patent No.: US 12,121,740 B2
(45) Date of Patent: Oct. 22, 2024

(54) WEARABLE ILLUMINATION DEVICE AND SYSTEM FOR INDUCING SYNTHESIS OF VITAMIN D IN THE BODY

(71) Applicants: KOREA ADVANCED INSTITUTE OF SCIENCE AND TECHNOLOGY, Daejeon (KR); SEOUL NATIONAL UNIVERSITY HOSPITAL, Seoul (KR); Gwangju Institute of Science and Technology, Gwangju (KR)

(72) Inventors: Seunghyup Yoo, Daejeon (KR); Jaehyeok Park, Daejeon (KR); Hanul Moon, Daejeon (KR); Sunhyoung Koo, Daejeon (KR); Changhun Seok, Daejeon (KR); Dongho Choi, Daejeon (KR); Hyuk Joo Lee, Seongnam-si (KR); In-Young Yoon, Seongnam-si (KR); Jun Seok Ahn, Seongnam-si (KR); Ji Su Choi, Seongnam-si (KR); Jung Kyung Hong, Seongnam-si (KR); Tae Kim, Gwangju (KR); Jiseung Kang, Gwangju (KR); Jieun Jung, Gwangju (KR)

(73) Assignees: KOREA ADVANCED INSTITUTE OF SCIENCE AND TECHNOLOGY, Daejeon (KR); SEOUL NATIONAL UNIVERSITY HOSPITAL, Seoul (KR); GWANGJU INSTITUTE OF SCIENCE AND TECHNOLOGY, Gwangju (KR)

(*) Notice: Subject to any disclaimer, the term of this patent is extended or adjusted under 35 U.S.C. 154(b) by 177 days.

(21) Appl. No.: 17/586,946

(22) Filed: Jan. 28, 2022

(65) Prior Publication Data
US 2022/0241606 A1 Aug. 4, 2022

(30) Foreign Application Priority Data

Jan. 29, 2021 (KR) .......................... 10-2021-0012831
Jan. 27, 2022 (KR) .......................... 10-2022-0012717

(51) Int. Cl.
*A61N 5/06* (2006.01)
(52) U.S. Cl.
CPC .......... *A61N 5/06* (2013.01); *A61N 2005/0645* (2013.01); *A61N 2005/0653* (2013.01); *A61N 2005/0661* (2013.01)
(58) Field of Classification Search
CPC .............. A61N 5/06; A61N 2005/0645; A61N 2005/0653; A61N 2005/0661; A61N 5/0613
See application file for complete search history.

(56) References Cited

U.S. PATENT DOCUMENTS 6,290,713 B1\* 9/2001 Russell ................ A61N 5/0616
607/91
2019/0099613 A1 4/2019 Estes et al.
(Continued)

FOREIGN PATENT DOCUMENTS

KR 10-2015-0033032 4/2015
KR 10-2015-0082761 7/2015
(Continued)

OTHER PUBLICATIONS

T. A. Kalajian et al., "Ultraviolet B Light Emitting Diodes (LEDs) Are More Efficient and Effective in Producing Vitamin D3 in Human Skin Compared to Natural Sunlight", Scientific Reports, vol. 7, p. 11489 (2017), Sep. 2017.

*Primary Examiner* — Yingchuan Zhang
*Assistant Examiner* — Sebastian X Lukjan
(74) *Attorney, Agent, or Firm* — LEX IP MEISTER, PLLC

(57) ABSTRACT

A system for inducing synthesis of Vitamin D in a body includes a wearable illumination device formed in a struc-
(Continued)

ture that is wearable on the body, and including a plurality of light sources configured to radiate an ultraviolet light to a skin of a worn part; and a control device connected to the plurality of light sources and configured to drive the plurality of light sources to radiate the ultraviolet light, wherein the wearable illumination device includes a light diffusion panel configured to equalize an irradiance of the ultraviolet light reaching the skin by causing diffusion of the ultraviolet light radiated from the plurality of light sources.

13 Claims, 15 Drawing Sheets

(56) References Cited

U.S. PATENT DOCUMENTS

| 2019/0117992 | A1* | 4/2019 | Iguchi | A61N 5/0621 |
| 2020/0101310 | A1* | 4/2020 | Marmur | A61Q 19/08 |
| 2021/0205632 | A1* | 7/2021 | Xu | A61N 5/062 |

FOREIGN PATENT DOCUMENTS

| KR | 10-2016-0033326 | 3/2016 |
| KR | 10-2016-0121153 | 10/2016 |
| KR | 10-2019-0052092 | 5/2019 |
| KR | 10-2020-0022767 | 3/2020 |
| KR | 10-2020-0042649 | 4/2020 |

* cited by examiner

WEARABLE ILLUMINATION DEVICE AND SYSTEM FOR INDUCING SYNTHESIS OF VITAMIN D IN THE BODY

CROSS-REFERENCE TO RELATED APPLICATION

This application claims priority to and the benefit of Korean Patent Application No. 10-2021-0012831 filed in the Korean Intellectual Property Office on Jan. 29, 2021, and Korean Patent Application No. 10-2022-0012717 filed in the Korean Intellectual Property Office on Jan. 27, 2022, the entire contents of which are incorporated herein by reference.

BACKGROUND

(a) Field

The present disclosure relates to a wearable illumination device and a system for inducing synthesis of Vitamin D in a body.

(b) Description of the Related Art

It is known that when the human body is exposed to sunlight in an appropriate dose every day, most of the Vitamin D3 necessary for metabolism can be synthesized naturally in the body by ultraviolet B components in the sunlight.

Vitamin D deficiency is a worldwide phenomenon due to the lack of a sunlight exposure for modern people who work mainly indoors. The total energy of ultraviolet B (UVB) band in sunlight is relatively small compared to a visible light or near-infrared light band, and thus exposure of sunlight for several hours is required. However, modern people often use sunblock at outdoors, which reduce UVB exposure by sunlight and thus the Vitamin D deficiency may become more severe.

It is also difficult to meet the daily requirement of Vitamin D from food intake. For people those who cannot get adequate exposure to sunlight, dietary Vitamin D supplement has been required to prevent Vitamin D deficiency.

However, there are concerns about possible side effects of taking high concentration of dietary Vitamin D supplements, which may cause initial overshoot of serum Vitamin D level.

In addition to the dietary Vitamin D supplements, many studies have been conducted on phototherapy device that allows synthesis of Vitamin D in the body using artificial light sources. The phototherapy device irradiates ultraviolet light to the human skin to induce natural synthesis of Vitamin D in the body.

It is known that an amount of synthesis of Vitamin D per unit area by UVB light is proportional to the total energy delivered per unit area (optical dose). Accordingly, for a given UVB irradiance, which corresponds to the energy incident on the skin per unit area per unit time of UVB light, the required optical dose may be achieved by controlling the exposure time. If the emission spectrum of a light source of the same optical power is limited to UVB, the amount of Vitamin D synthesis that takes several hours of exposure to the sunlight may be achieved in a very short time around a few minutes, leading to supplement of Vitamin D without interfering with a busy lifestyle of modern people.

However, it is known that the ultraviolet wavelength light may induce erythema on the skin in the short term, and pigmentation or skin cancer in the long term, due to the characteristic of a high energy per photon compared to the visible spectrum, when exposed to an excessive amount. In order to prevent these side effects, in the case of ultraviolet phototherapy device, compared to treatment of visible light or infrared ray, light should not be concentrated on a specific area of the skin, and thus it is important to ensure uniform light irradiation so that any local spot does not exceed the limit energy dose.

In order to achieve uniform light irradiation, a technology capable of realizing an intrinsic surface light source is required. Organic light-emitting diodes (OLEDs), perovskite light-emitting diodes (PeLEDs), and quantum dot light-emitting diodes (QLEDs) are known as good examples. However, in implementing the ultraviolet light source, all of these methods have not yet overcome a challenge that a light emitting material itself can be easily degraded by irradiation of ultraviolet light or high energy photons. Therefore, solving durability problem should be preceded in order to implement the aforementioned light source technologies to phototherapy devices for synthesis of Vitamin D for stable and long-term use. As such, due to difficulty of developing a surface light source emitting ultraviolet B, development of ultraviolet phototherapy devices has been relatively slower than those of visible light or red light.

There are some commercialized ultraviolet phototherapy devices, which are whole-body-illuminating light source devices using multiple gas discharge lamps. Because gas discharge lamp-based ultraviolet light sources have large volume and are not intrinsically uniform, a large distance, for example, more than 1 m away from the light source, may be desired for uniform phototherapy. In this case, large distance solves the problems of low-temperature local burns due to heat dissipation from concentrated light source and light non-uniformity problems which may cause local erythema, but there is a problem in that phototherapy efficiency is low because light is lost to an ambient rather than a target human body. In addition, it is necessary to take a special precaution such as wearing protective goggles to protect the eyes from ultraviolet light that spreads to the surroundings.

As an alternative to the gas discharge lamp, there is a method using an inorganic light-emitting diode (LED) based on a group III-V compound semiconductor. However, since the inorganic LED is in the form of quasi-point light source, a distance to spread the light may not necessarily be sufficient when light emits from a close distance to the skin, and thus the light is concentrated on a region around the LED, which may cause a side effect according to irradiation of an excessive dose of energy to occur in the area. For this reason, there is a trade-off relationship; to spread out the light distribution, the overall size of the device should increase, which then reduces portability and space utilization.

The above information disclosed in this Background section is only for enhancement of understanding of the background of the invention, and therefore it may contain information that does not form the prior art that is already known in this country to a person of ordinary skill in the art.

SUMMARY

The present disclosure has been made in an effort to provide a wearable illumination device and a system having advantages of inducing synthesis of Vitamin D in the body by using an ultraviolet B light source. An exemplary embodiment of the present disclosure provides a wearable illumination device and a system for inducing synthesis of Vitamin D in the body, thereby enabling easy wearing on arms or legs in phototherapy using an ultraviolet B light source, maintaining a portable form, and simultaneously realizing uniform light emission with fewer light-emitting diodes (LEDs) even at a distance close to the skin.

Another embodiment of the present disclosure provides a wearable illumination device including a housing formed in a structure that is wearable on a body, a light source installed in an inner part of the housing to radiate an ultraviolet light for inducing Vitamin D in the body to a skin of the body accommodated in the housing; and a light diffusion panel located between the light source and the skin, and configured to equalize an irradiance of the ultraviolet light reaching the skin by causing diffusion of the ultraviolet light radiated from the light source.

In the light diffusion panel, three-dimensional (3D) patterns that promote light diffusions on an interface where the ultraviolet light is incident from the light source may be formed.

The 3D pattern may include a micro-pattern of an inwardly concave shape toward the light diffusion panel on the interface.

The light diffusion panel may include light scattering particles having refractive indexes different from that of the light diffusion panel and causing the light diffusion of the ultraviolet light.

The light diffusion panel may be made of a material having an ultraviolet ray transmittance equal to or greater than that of a polydimethylsiloxane (PDMS) material.

The wearable illumination device may further include at least one spacer located between the housing and the light diffusion panel to separate the light source from the skin by a predetermined distance.

The at least one spacer may have one side connected to the housing and the other side connected to the light diffusion panel and may be formed at a height by which the light source is separated from the skin by the predetermined distance.

The housing may be made of a flexible material so as to wrap an arm of the body, have at least one hook-and-loop fastener attached to a fastening unit formed on one side and a fastening unit formed on the other side fastened to the at least one hook-and-loop fastener, and configured in a structure that wraps around the arm and is detachable on the arm.

The housing may be integrally formed or assembled with a light blocking unit for shielding the ultraviolet light to prevent the ultraviolet light from leaking to an outside.

The light source may include plurality of light emitting diode (LED) devices, and the LED devices may be connected to an electrode wiring in series or in parallel on a flexible printed circuit board (FPCB), a connector on electrode wiring may be connected to which a control device supplying a current to the multiple light sources, and a heat sink for minimizing a heat transfer to the skin may be installed at a point near a point where the plurality of light sources are installed in a rear surface of the FPCB.

Yet another embodiment of the present disclosure provides a system for inducing synthesis of Vitamin D in a body including a wearable illumination device formed in a structure that is wearable on the body, and including a plurality of light sources configured to radiate an ultraviolet light to a skin of a worn part; and a control device connected to the plurality of light sources and configured to drive the plurality of light sources to radiate the ultraviolet light, wherein the wearable illumination device includes a light diffusion panel configured to equalize an irradiance of the ultraviolet light reaching the skin by causing diffusion of the ultraviolet light radiated from the plurality of light sources.

The control device may include a current supply module connected to the plurality of light sources and configured to supply a current supplied from a power supply unit to the plurality of light sources, and a control unit connected to the current supply module and configured to control a current supply of the current supply module, wherein the control unit may be configured to, after the current supply of the current supply module starts, when a preset time elapses, stop the current supply.

The wearable illumination device may include an optical sensor configured to measure an irradiance of the ultraviolet light radiated to the skin, and wherein the control unit may be configured to receive an irradiance measurement value of the ultraviolet light from the optical sensor, when the irradiance measurement value exceeds a set maximum irradiance, adjust at least one of a current output amount of the current supply module, a current output time, the number of light sources to which the current is supplied, and positions of the light sources, and reduce the irradiance of the ultraviolet light radiated to the skin.

The control device may include a user manipulation unit configured to receive identification information of a user and a driving command of the wearable illumination device; and a control unit configured to check a last usage time by inquiring a previous usage record matching the received identification information of the user, and determine whether to drive the wearable illumination device based on whether a determined time period has elapsed from the last usage time, wherein the control unit may be configured to, when it is determined to drive the wearable illumination device, match a usage record with the received identification information of the user and store the usage record including a driving start time and a driving end time.

According to the embodiment, even when the light source is disposed at a close distance to the skin, there is an effect of reducing side effects such as erythema formation that may occur due to concentration of ultraviolet ray on a specific area of the skin.

In addition, it is possible to shorten the distance that causes a uniform irradiation of light on the skin with respect to the same number of light sources, making it possible to reduce the size of the device, and by using only the ultraviolet B light source necessary for synthesis of Vitamin D, synthesis of Vitamin D may be derived even with irradiation for a significantly lower time compared to exposure to sunlight.

Alternatively, fewer light sources may be used to achieve the same light irradiance uniformity criteria, thereby reducing material and production costs, and ultraviolet B light is irradiated only to the part where the wearable illumination device according to the embodiment is worn, thereby providing convenience of not having to cover the eyes with UV protection goggles.

DETAILED DESCRIPTION OF THE EMBODIMENTS

Figure 1:
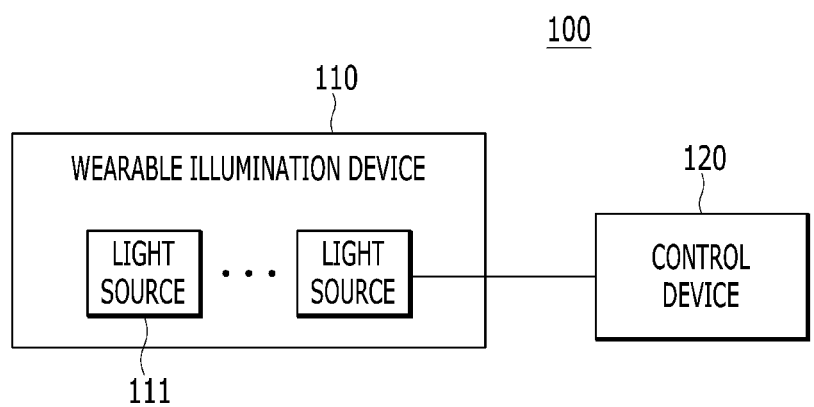
FIG. 1 is a schematic configuration diagram of a system for inducing synthesis of Vitamin D in the body according to an embodiment.

Hereinafter, with reference to the accompanying drawings, the present disclosure will be described in detail such that those skilled in the art may easily carry out the present disclosure with respect to the embodiments of the present disclosure. However, the present disclosure may be embodied in many different forms and is not limited to the embodiments set forth herein. In addition, to clearly describe the present disclosure, parts unrelated to the descriptions are omitted, and the same or similar elements are denoted with the same reference numerals throughout the specification.

Throughout the specification, unless explicitly described to the contrary, the word "comprise", and variations such as "comprises" or "comprising", will be understood to imply the inclusion of stated elements but not the exclusion of any other elements.

In addition, the terms "-er", "-or", and "module" described in the specification mean units for processing at least one function and operation, and may be implemented by hardware components or software components, and combinations thereof.

In the present specification, "transmission or provision" may include not only direct transmission or provision, but also transmission or provision indirectly through another device or using a detour path.

In the present specification, expressions described in the singular may be construed in the singular or plural unless an explicit expression such as "one" or "single" is used.

In the present specification, regardless of the drawings, the same reference numerals refer to the same elements, and "and/or" includes each of the mentioned elements and all combinations of at least one of the mentioned elements.

In the present specification, the terms including ordinal numbers such as first, second, etc. may be used to describe various elements, but the elements are not limited by the terms. The terms are used only for the purpose of distinguishing one element from another element. For example, without departing from the scope of the present disclosure, a first element may be named as a second element, and similarly, the second element may also be named as the first element.

FIG. 1 is a schematic configuration diagram of a system for inducing synthesis of Vitamin Din the body according to an embodiment.

Referring to FIG. 1, the system 100 for inducing synthesis of Vitamin D in the body includes a wearable illumination device 110 and a control device 120.

The wearable illumination device 110 has a structure that is wearable on the human body and is portable.

The wearable illumination device 110 includes a plurality of light sources 111 irradiating light having an ultraviolet wavelength to the skin of a wearing body part.

The light source 111 radiates light of a wavelength of ultraviolet B (280 to 320 nm).

As the light source 111, an inorganic light-emitting diode (hereinafter, collectively referred to as an LED) device may be used. In the case of the LED device, durability and stability are guaranteed as an ultraviolet B light source, and because the light source has a small full width at half maximum (FWHM) and emits only a wavelength that is efficient for synthesis of Vitamin D, a phototherapy efficiency is high. In addition, compared to a lamp, the LED device has a small size and generates less heat, making it possible to miniaturize the light source, and thus it is possible to manufacture a portable phototherapy device in the form that is attachable to the skin.

The control device 120 is electrically connected to the plurality of light sources 111. The control device 120 drives the light source 111 by applying a forward potential to the light source 111 so that the light source 111 radiates light. The control device 120 may independently drive each of the plurality of light sources 111.

According to an embodiment, a subgroup may be formed in which the plurality of light sources 111 are grouped in units of a predetermined number, and the plurality of light sources 111 in the subgroup may be connected in series or in parallel. At this time, the control device 120 may minimize the number of wirings in a cable connecting the wearable illumination device 110 and the control device 120, by driving the light sources 111 in units of subgroups. For example, when driving the light sources 111 in units of light sources, wires are required by the number of light sources, but when the light sources are grouped into a predetermined number and driven in units of groups, the number of wires may be reduced by the number of groups.

Figure 2:
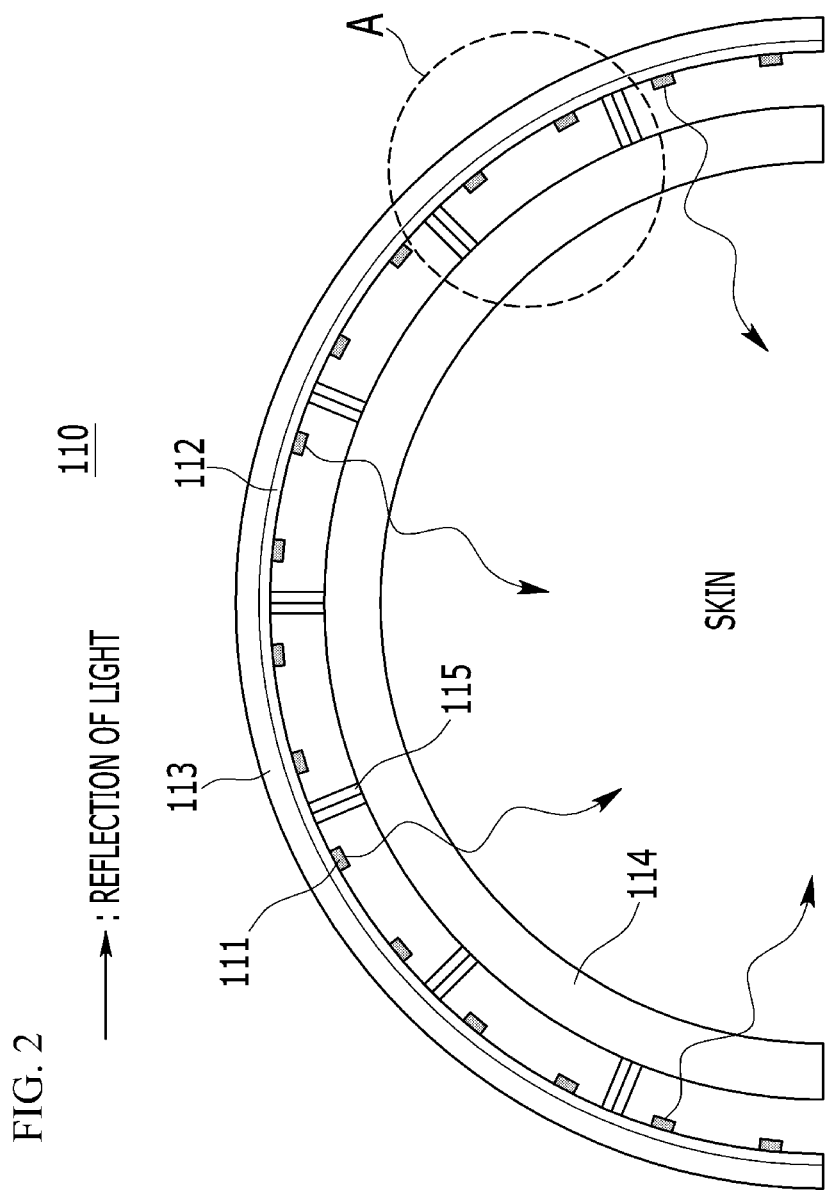
FIG. 2 shows a schematic configuration of a wearable illumination device according to an embodiment.
Figure 3:
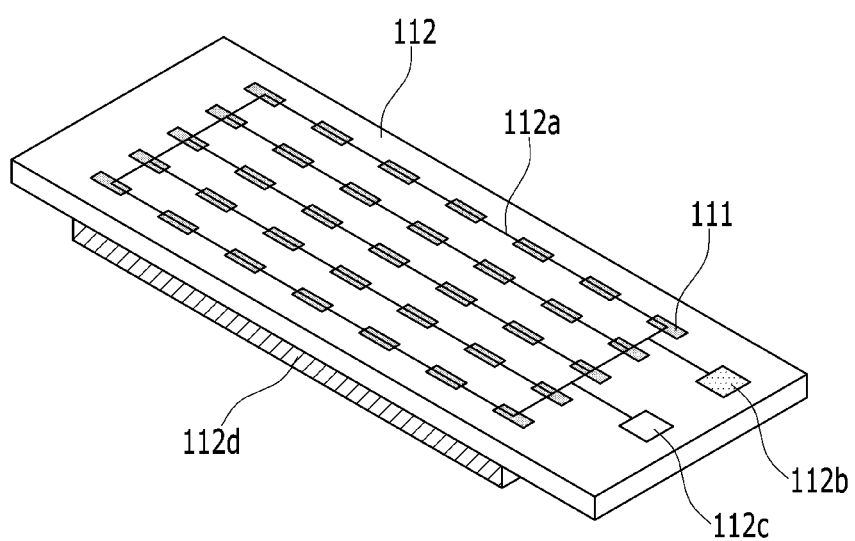
FIG. 3 is a diagram showing a configuration of a substrate on which a plurality of light sources are mounted according to an embodiment.
Figure 4:
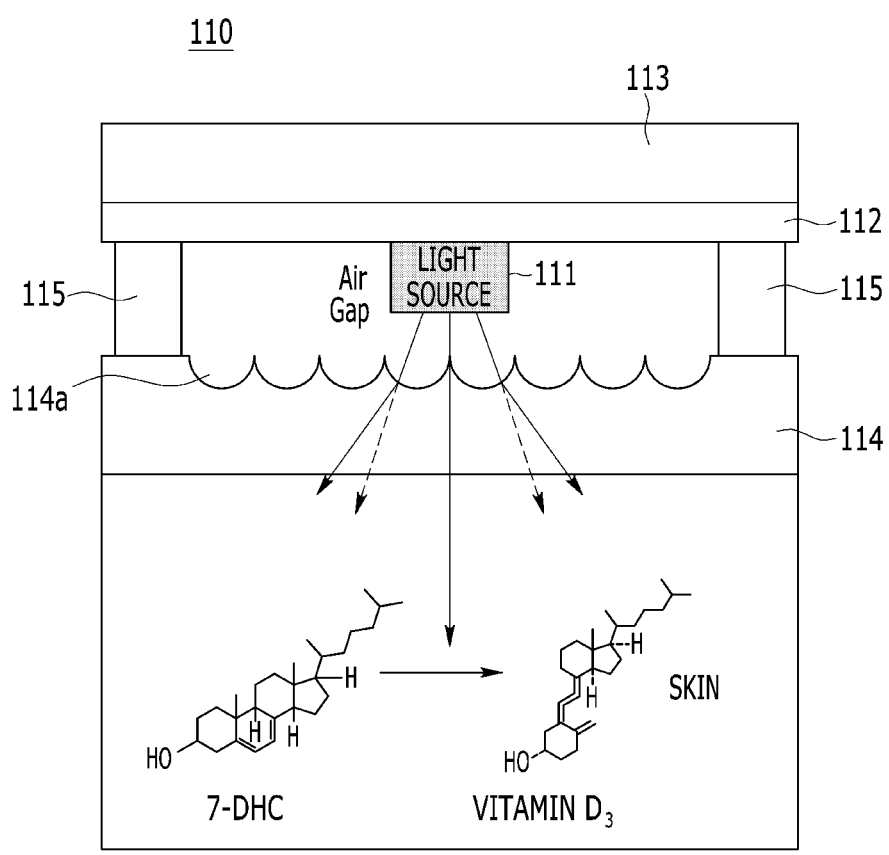
FIG. 4 is an enlarged side view of part 'A' of FIG. 2 according to an embodiment.
Figure 5:
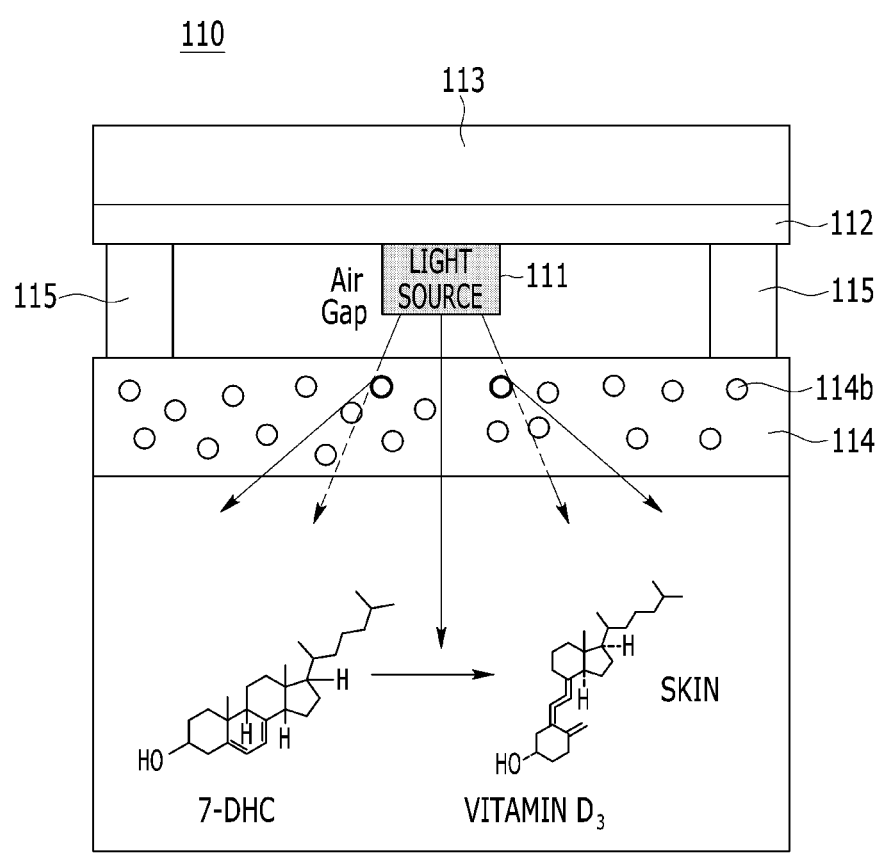
FIG. 5 is an enlarged side view of part 'A' of FIG. 2 according to another embodiment.

FIG. 2 shows a schematic configuration of a wearable illumination device according to an embodiment, FIG. 3 is a diagram showing a configuration of a substrate on which a plurality of light sources are mounted according to an embodiment, FIG. 4 is an enlarged side view of part 'A' of FIG. 2 according to an embodiment, and FIG. 5 is an enlarged side view of part 'A' of FIG. 2 according to another embodiment.

Referring to FIG. 2, the wearable illumination device 110 may include the plurality of light sources 111, a substrate 112 on which the plurality of light sources 111 are mounted, a housing 113, and a light diffusion panel 114, and a plurality of spacers 115.

The plurality of light sources 111 may include a plurality of light emitting diode (LED) devices emitting an ultraviolet B region and may be mounted on the substrate 112, and the substrate 112 on which the plurality of light sources 111 are mounted may be installed inside the housing 113.

The substrate 112 may be configured as an LED array substrate in which the plurality of light sources 111 emitting the ultraviolet B region are arranged.

According to an example, the light source 111 may include a plurality of LED devices arranged in parallel. The plurality of LED devices may be arranged in a regular grid form or irregular pattern for efficient and safe phototherapy. In addition, the LED array substrate may be configured to retain its form when attached to the human skin.

Referring to FIG. 3, the plurality of light sources 111 are arranged in a grid form on the substrate 112 and configured to radiate light toward the skin from a certain distance or more, thereby making it possible to obtain uniformity similar to that of a surface light source. The substrate 112 may be a flexible printed circuit board (hereinafter, collectively referred to as 'FPCB').

In the substrate 112, an electrode wiring 112a is installed to provide a potential necessary for operation to a negative electrode and a positive electrode of the LED, and a connector 112b to which a power cable connected to an external power supply device, that is, the control device 120, is connected is installed and may operate as an electrode pad. In addition, the substrate 112 may include an optical sensor 112c.

When a LED light source converts electrical energy into light energy, because efficiency of the electrical energy is usually not 100%, the electrical energy is partially lost as thermal energy. Therefore, the wearable illumination device 110 may include a heat dissipating member or a heat dissipating device that maintains a temperature equal to or less than 40 degrees during the operation of the light source 111 in order to reduce a risk of low temperature burns due to heat generated from the light source 111.

As an example of a heat dissipating member or a heat dissipating device, a small fan may be installed near a rear surface of the light source 111, but the fan requires a separate power supply for driving, generates noise, and is an obstacle to miniaturization of the wearable illumination device 110. In order to solve this and minimize heat transfer to the skin, a heat sink 112d may be installed near the rear surface of the light source 111. The heat sink 112d may effectively realize heat dissipation while maintaining miniaturization of the wearable illumination device 110. A large area of the rear surface of the substrate 112 on which the plurality of light sources 111 are disposed is formed of a conductor such as a copper film, and a part of each light source 111 and the copper film of a rear surface of the substrate 112 may be thermally connected to each other via a through conductor. At this time, the through conductor is connected while preventing a short circuit of the light source 111 by preventing electrical contact between the negative electrode and the positive electrode of the light source.

An optical sensor 112c may be installed on the substrate 112. The optical sensor 112c may measure irradiance of ultraviolet light radiated to the skin and transmit a measurement value to the wearable illumination device 110.

The housing 113 is an exterior of the wearable illumination device 110 and is formed in a structure that is wearable on the human body.

The housing 113 may have a structure that is worn on the human body and is detachable.

The housing 113 may be configured to maintain its form when attached to the human skin. The housing 113 may be configured in a flat or curved shape to fit a body part to be attached.

The housing 113 may be made of a flexible material that is wearable on the human body. For example, the housing 113 may use a flexible polymer material such as polyurethane, but is not limited thereto.

The housing 113 may include light blocking units (113a in FIGS. 6 and 7, 113b in FIGS. 7, 10, and 11) so that ultraviolet light does not spread to parts other than the body part which is a light irradiation part in order to prevent side effects caused by the ultraviolet light. The light blocking units 113a and 113b are materials that absorb ultraviolet rays, may take the form of a physical blocking film, and may be integrally formed with or assembled and integrated into the housing 113.

The light diffusion panel 114 may be located inside the housing 113 in which the light source 111 is installed, and may be in close contact with the human skin. The light diffusion panel 114 serves to equalize an irradiance of the light reaching the skin, by causing diffusion of light irradiated from the light source 111 between the light source 111 and the skin.

The better, the light diffusion panel 114 has a higher ultraviolet rays transmittance so as to reduce loss of ultraviolet ray light from the light source 111, and it is advantageous to have flexibility so that the light diffusion panel 114 may be deformed according to a shape of the body part to be worn.

In this regard, the light diffusion panel 114 may be made of a polydimethylsiloxane (PDMS) material having a higher ultraviolet rays transmittance than a normal transparent plastic material and excellent flexibility.

However, the light diffusion panel 114 is not limited to the PDMS material, and various materials having the ultraviolet rays transmittance higher than that of the PDMS material may be used.

When there is no transmissive ultraviolet light diffusion panel 114, the irradiance of light reaching the skin is not uniform. However, when the light diffusion panel 114 is present, the light diffusion panel 114 improves the irradiance uniformity of the light reaching the skin, thereby reducing concentration of ultraviolet rays in a local area, and thus side effects such as erythema formation may be reduced.

The light diffusion panel 114 transmits the ultraviolet light radiated from the light source 111 and is configured to cover the entire irradiation area of the light. The light diffusion panel 114 may improve light uniformity at a short distance between the light source 111 and the skin.

An air gap having a predetermined thickness is formed between the housing 113 and the light diffusion panel 114. Accordingly, the ultraviolet light radiated from the light source 111 is introduced into the light diffusion panel 114 through the air gap, and the light passing through the inside of the light diffusion panel 114 is radiated to the skin.

According to an embodiment, as shown in FIG. 4, a three-dimensional (3D) pattern 114a is formed on one side or both sides of a surface of the light diffusion panel 114 to induce light diffusion. According to an example, the 3D pattern 114a may be concave micropatterns. A concave portion includes air and has a refractive index close to 1, and the light diffusion panel 114 has a refractive index greater than 1 so that a refraction phenomenon according to Snell's law occurs on a concave-shaped interface to refract a direction of light incident from the light source 111 and provide an effect of spreading the light.

According to another embodiment, as shown in FIG. 5, the light diffusion panel 114 may include light scattering particles 114b that cause light diffusion therein. The light scattering particles 114b are particles having refractive indexes different from that of the light diffusion panel 114, and may be randomly arranged in the light diffusion panel 114. A degree of diffusion of the light scattering particles 114b may be adjusted according to the concentration in the light diffusion panel 114. The light scattering particles 114b may be nanoparticles such as $SiO_2$ or $TiO_2$, and shape of air bubbles, that is, pores, may provide the same effect.

The plurality of spacers 115 may be formed between the housing 113 and the light diffusion panel 114. The plurality of spacers 115 are formed in a structure in which one side is connected to the substrate 112 located inside the housing 113 and the other side supports the light diffusion panel 114. In this regard, the plurality of spacers 115 may have a cubic column shape.

The plurality of spacers 115 are formed at a height by which the light source 111 may be separated from the skin by a predetermined distance. In a state in which the wearable illumination device 110 is attached to or mounted on the skin, the light source 111 is preferably set at a maximum distance of less than 5 cm from the skin. Accordingly, the plurality of spacers 115 having a height capable of maintaining such a maximum distance of less than 5 cm may be formed. At this time, in order to miniaturize the housing 113, a height of the spacer 115 may be configured to be about 1 cm.

The ultraviolet light radiated from the light source 111 penetrates the light diffusion panel 114 and is irradiated to the skin at a uniform irradiance to synthesize Vitamin D in the body. It is known that synthesis of Vitamin D in the body is a mechanism in which 7-dihydrocholesterol, that is, 7-DHC or provitamin D3, which is naturally present between epidermis and dermis, receives ultraviolet light, passes through various forms of intermediate substances, and is finally converted into Vitamin D. Through in vitro solution experiment, it was confirmed that when light of an ultraviolet B (280-320 nm) wavelength is irradiated to a 7-DHC material, this conversion may occur efficiently more than several tens of times compared to sunlight.

Figure 6:
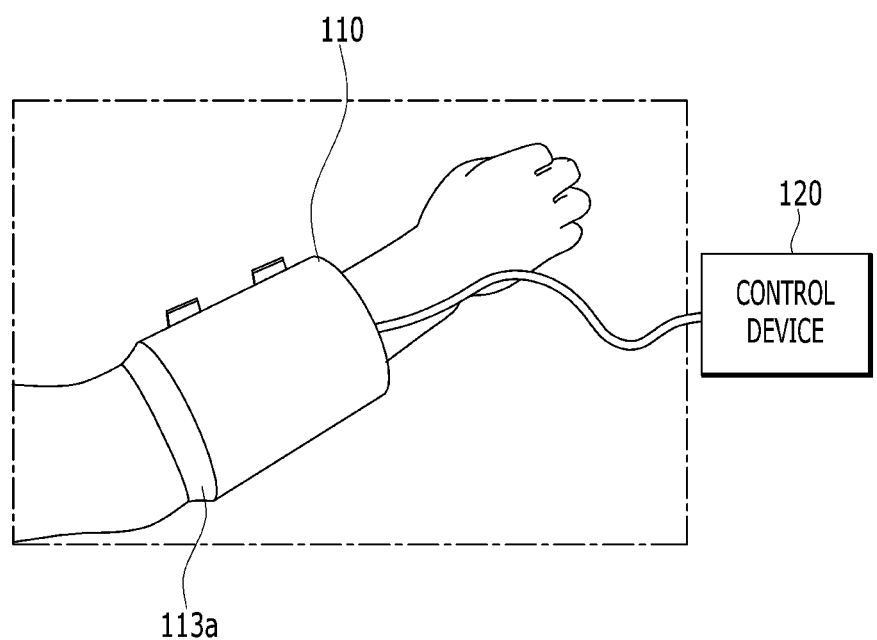
FIG. 6 is an exemplary view of a wearable illumination device worn on an arm according to an embodiment.
Figure 7:
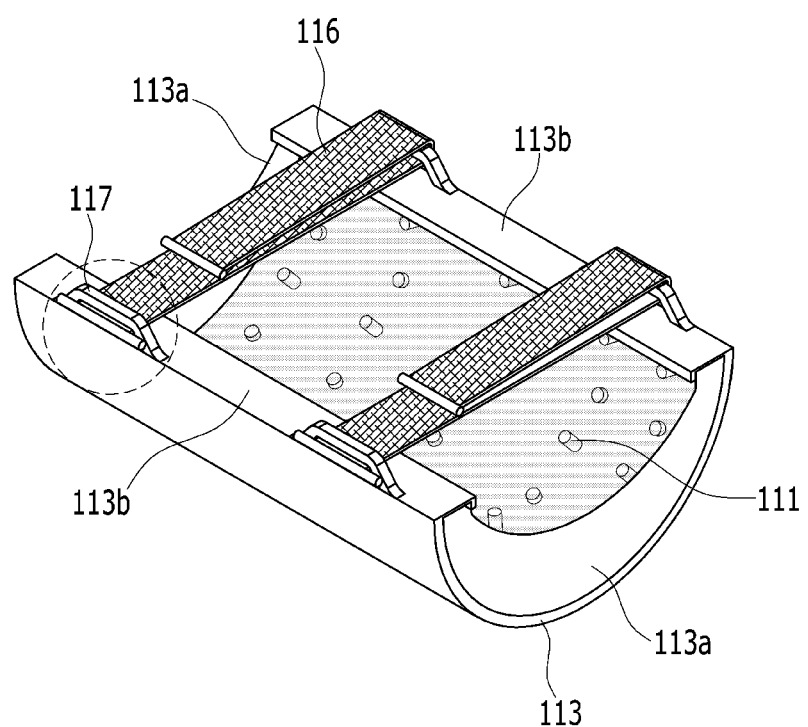
FIG. 7 is an exemplary configuration diagram of the wearable illumination device according to an embodiment.
Figure 8:
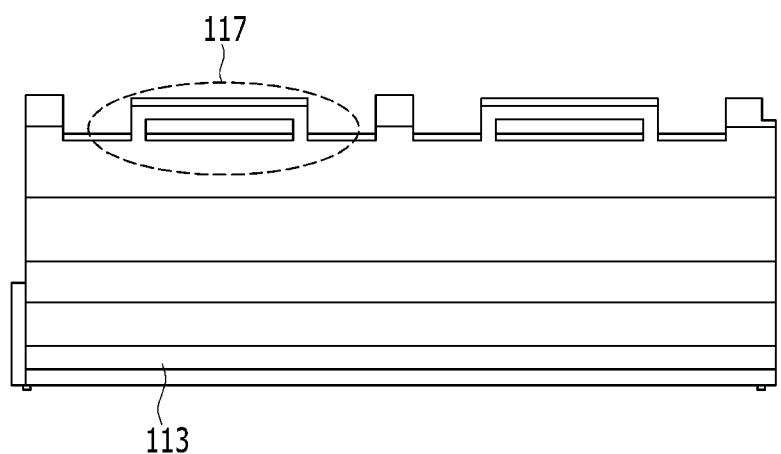
FIG. 8 is an enlarged side view of a fastening unit of FIG. 5.

FIG. 6 is an exemplary view of a wearable illumination device worn on an arm according to an embodiment, FIG. 7 is an exemplary configuration diagram of the wearable illumination device according to an embodiment, and FIG. 8 is an enlarged side view of a fastening unit of FIG. 5.

Referring to FIG. 6, the wearable illumination device 110 may be configured to wrap an arm of a human body. However, the wearable illumination device 110 is not limited to a form surrounding the arm, and may be configured in a form surrounding other parts of the body, such as a foot or calf.

A cable connected to the substrate 112 on which the light source 111 installed inside is mounted is exposed on one side of the wearable illumination device 110, and may be connected to the control device 120.

At this time, the housing (113 in FIGS. 2, 3, 4, and 5) may be made of a flexible material to wrap the arm of the human body.

Referring to FIG. 7, at least one hook-and-loop fastener 116 is attached to one side of the housing 113 in which the light source 111 is embedded, and at least one fastening unit 117 fastened to the at least one hook-and-loop fastener 116 may be formed in the other side of the housing 113.

The fastening unit 117 serves to fix the hook-and-loop fastener 116, and may be configured in the form of a buckling.

A separate light blocking unit 113a may be formed at a part of the housing 113 where the fastening unit 117 is not installed, that is, at a position where the arm comes out. The light blocking unit 113a shields an inner space formed by the arm and the housing 113 in a state where the light blocking unit 113a is integrally formed with the housing 113 and is worn on the arm to wrap around the housing 113, thereby preventing ultraviolet light irradiated to the arm from leaking to the outside.

At this time, a bending radius of the housing 113 may be adjusted to the size of the arm according to a degree of tightening of the hook-and-loop fastener 116. In this regard, the light blocking unit 113a may be made of a material that may be deformed, such as a stretchable band, so as to respond according to a degree of bending of the housing 113.

In addition, the light blocking unit 113b which is a protruding structure supporting the fastening unit 117 may have its edge in close contact with the arm when the wearable illumination device 110 is worn, thereby serving to block light to prevent the ultraviolet light from leaking.

Referring to FIG. 8, the fastening unit 117 may have a shape of a buckle ring. The hook-and-loop fastener (116 in FIG. 7) is inserted into a hole inside the buckle ring so that the housing 113 may be fixed to the arm.

As such, the wearable illumination device 110 may be formed in a structure that wraps around the arm and is detachably worn on the arm.

Figure 9:
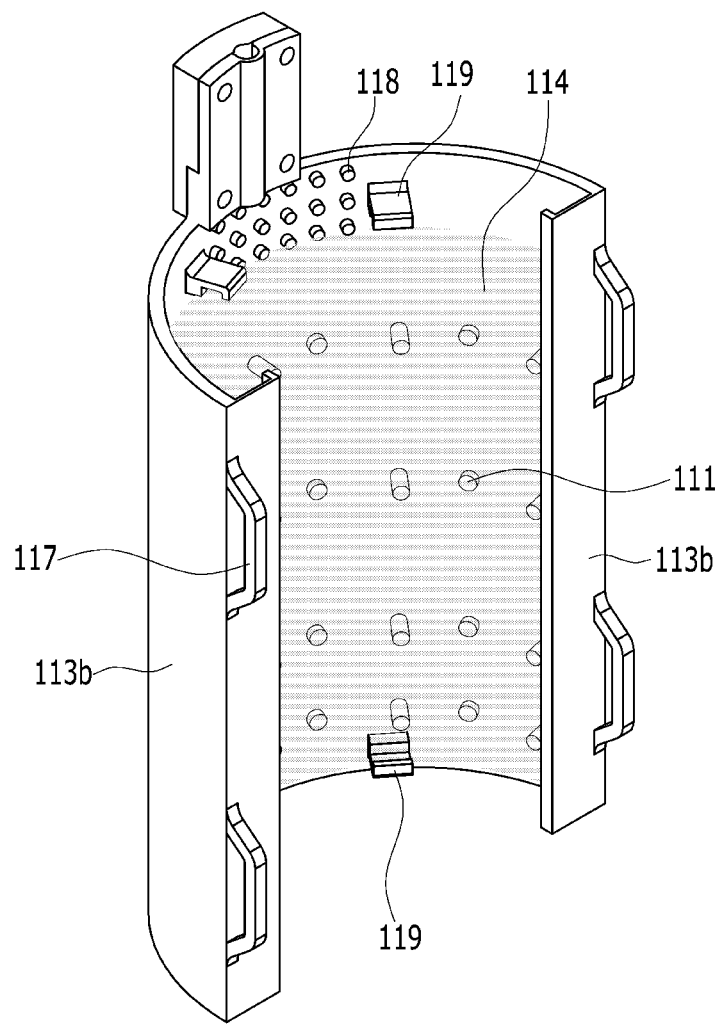
FIG. 9 is a cubic perspective view of a wearable illumination device according to another embodiment.
Figure 10:
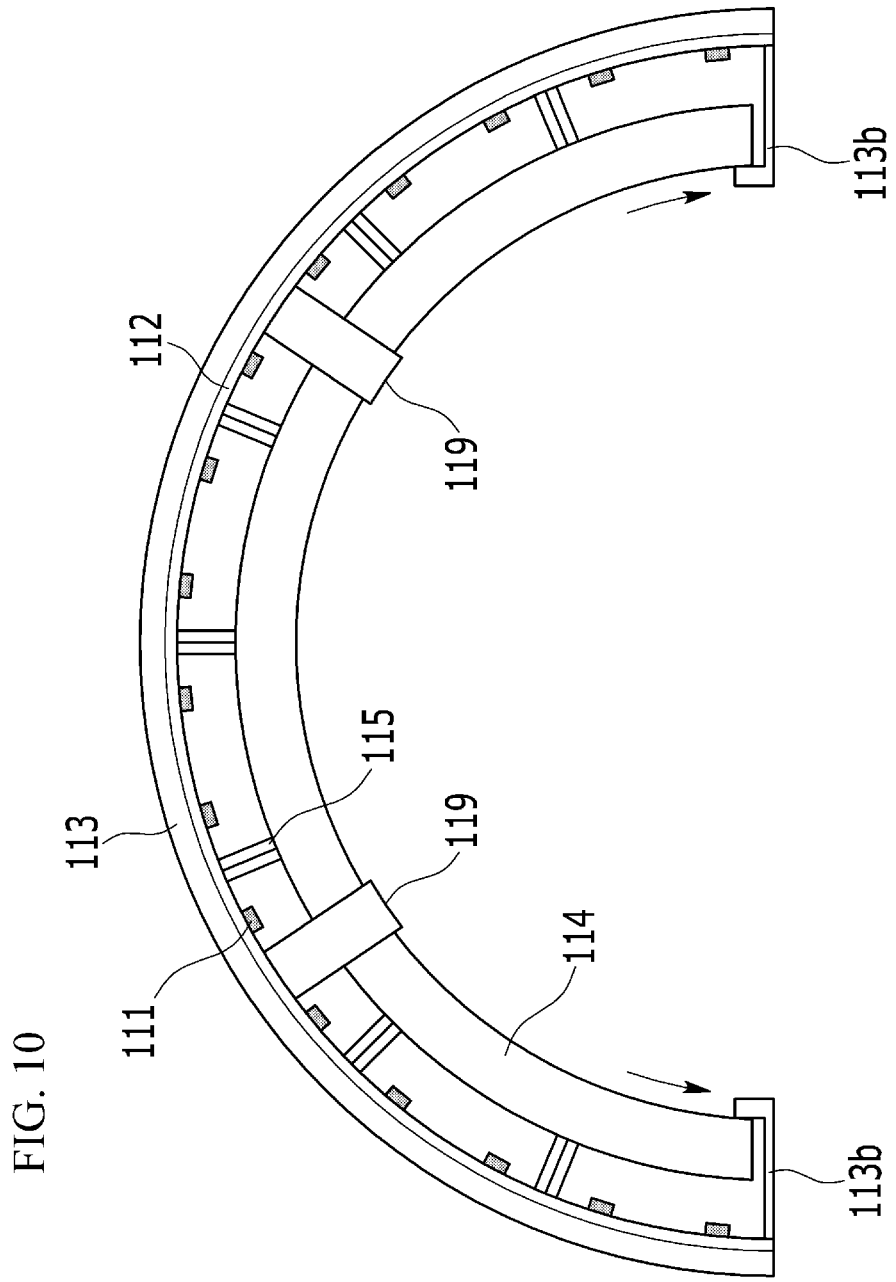
FIG. 10 shows a state before a light diffusion panel is accommodated in a light blocking unit according to an embodiment.
Figure 11:
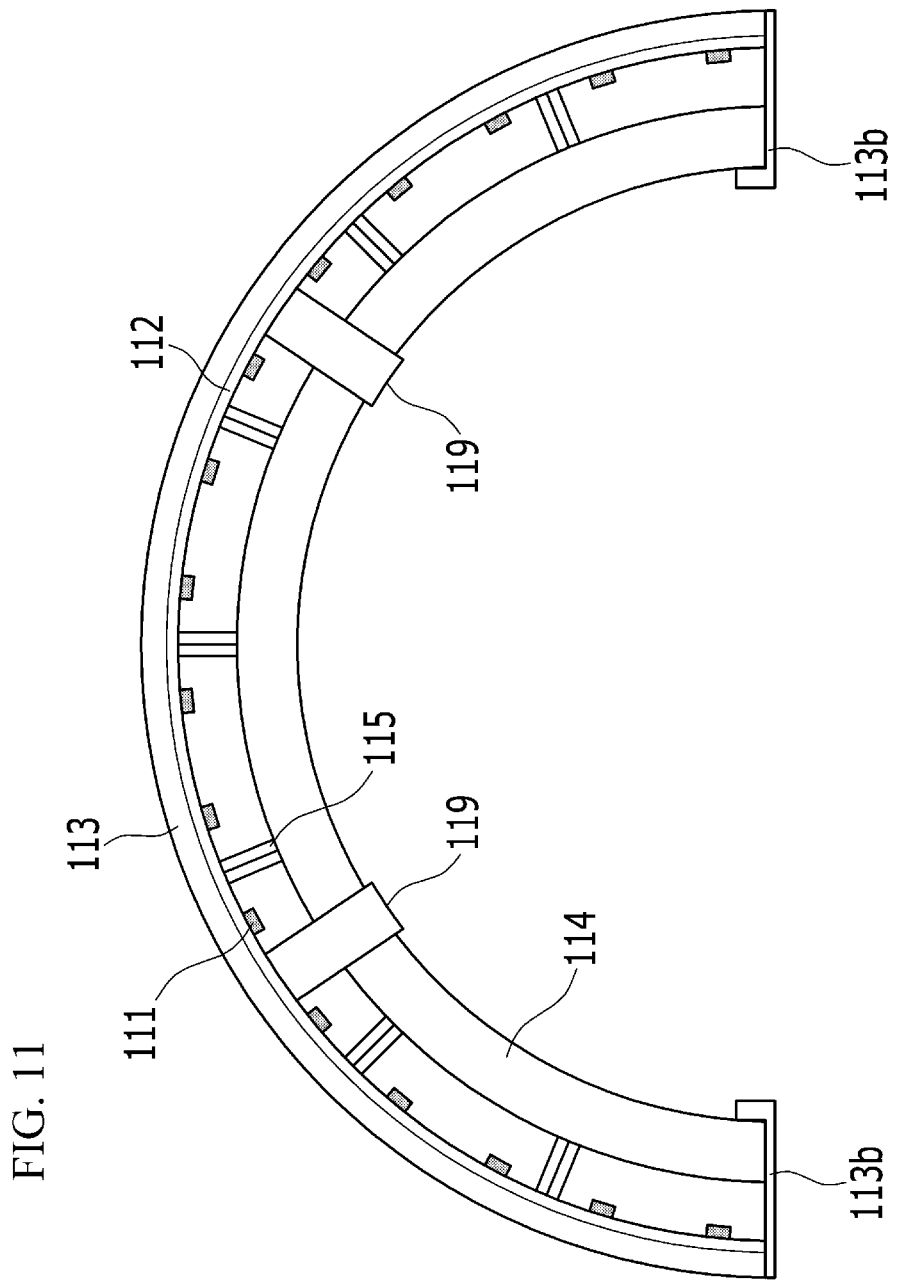
FIG. 11 shows a state after the light diffusion panel is accommodated in a light blocking unit according to an embodiment.

FIG. 9 is a cubic perspective view of a wearable illumination device according to another embodiment, FIG. 10 shows a state before a light diffusion panel is accommodated in the light blocking unit 113b according to an embodiment, and FIG. 11 shows a state after the light diffusion panel is accommodated in the light blocking unit 113b according to an embodiment.

Referring to FIG. 9, as described with reference to FIGS. 2 to 5, the plurality of spacers 115 are formed inside the housing 113 in close contact with the skin.

A plurality of fastening units 117 for fixing the hook-and-loop fastener (116 in FIG. 7) are formed on both ends of the housing 113.

A tension relieving structure may be formed in an inner upper end of the housing 113. The tension relieving structure may be a plurality of protrusions 118. When a cable drawn from the substrate 112 is tied to the protrusions 118 or fixed with an adhesive, etc., and is pulled from the outside of the housing 113, the tension relieving structure serves to relieve the tension so that the tension is not transmitted to a part where the substrate 112 and the cable are connected to each other.

Hooks 119 may be formed on upper and lower inner sides of the housing 113. These hooks 119 serve to fix the light diffusion panel 114 to the housing 113 to prevent the light diffusion panel 114 from sliding to the outside of the housing 113. Since the light diffusion panel 114 is not accommodated in the hooks 119 before the light diffusion panel 114 is in close contact with the skin, both upper and lower ends of the light diffusion panel 114 form a predetermined space with the hooks 119. In this state, when the wearable illumination device 110 is in close contact with the skin, the housing 113 is bent so that a curvature is changed. In this state, since the light diffusion panel 114 is not fixed to the spacers 115, the light diffusion panel 114 moves in a direction in which the hooks 119 are installed due to a difference in the radius of curvature and is in close contact with the hooks 119. Accordingly, since no additional shear stress is applied to the light diffusion panel 114, the light diffusion panel 114 may maintain a certain distance from the skin without being torn or twisted.

Also, referring to FIG. 10, the light blocking unit 113b described in FIG. 7 forms a predetermined space with the light diffusion panel 114 before the light diffusion panel 114 is in close contact with the skin. In this state, when the wearable illumination device 110 is in close contact with the skin, the light diffusion panel 114 is in close contact with the light blocking unit 113b as shown in FIG. 11. Accordingly, the light blocking unit 113b may block the ultraviolet light radiated from the light source 111 from being emitted to the outside.

Figure 12:
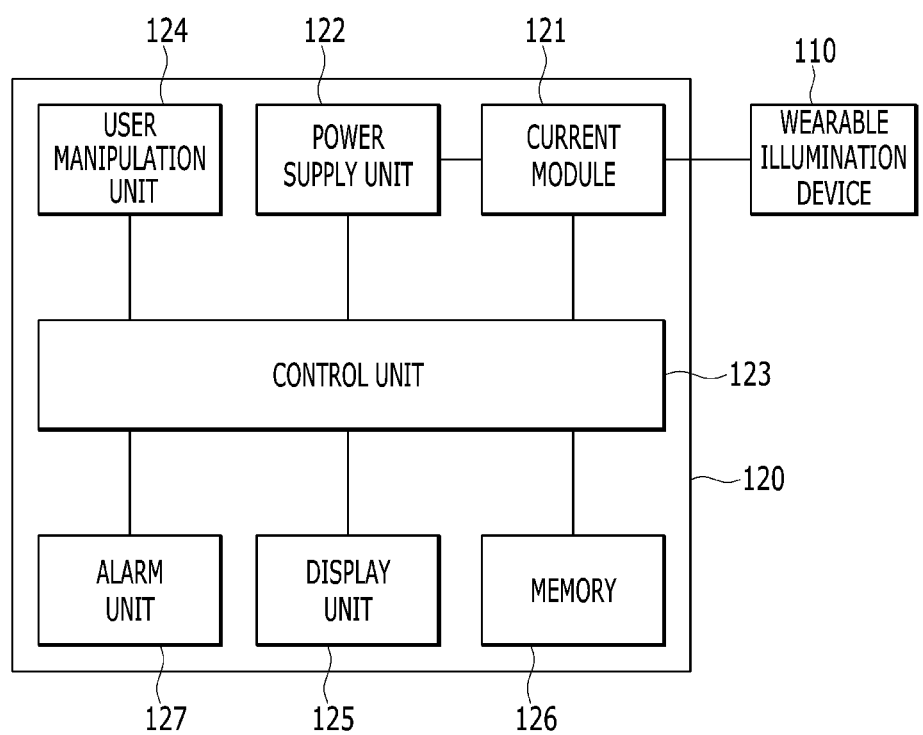
FIG. 12 is a block diagram showing a configuration of a control device according to an embodiment.

FIG. 12 is a block diagram showing a configuration of a control device according to an embodiment.

Referring to FIG. 12, the control device 120 may include a current supply module 121, a power supply unit 122, a control unit 123, a user manipulation unit 124, a display unit 125, a memory 126, and an alarm unit 127.

The current module 121 is electrically connected to the plurality of light sources 111 of the wearable illumination device 110. The current module 121 supplies a current supplied from the power supply unit 122 to the plurality of light sources 111 under the control of the control unit 123 to emit light of the plurality of light sources 111.

According to an embodiment, the current module 121 may supply the current to the plurality of light sources 111 connected through a cable.

According to another embodiment, the current module 121 may supply the current to the plurality of light sources 111 by using a wireless power transmission method. The control device 120 may remotely drive the light source 111 by using wireless power transmission.

The power supply unit 122 may include an adapter that converts external power to be suitable for driving the light source 111 or a battery capable of supplying power by itself.

The control device 120 may drive the light source 111 by using DC power or AC power.

The control device 120 may use an adapter that converts external power into DC power having a potential suitable for driving the light source 111 or an external battery capable of supplying power by itself.

The control unit 123 may control a light irradiation intensity, a light irradiation time, a light irradiation time series routine, light irradiation start and end, etc. of the light source 111. Here, the light irradiation time series routine means a process of light irradiation and light interruption according to time.

The control unit 123 executes a stored light source driving control program, and may be, for example, a microcontroller unit (MCU). The control unit 123 may control whether light is irradiated to the skin, by determining whether to supply the current to the current module 121 according to a user command transmitted from the user manipulation unit 124.

In this regard, a relay switch or a semiconductor type voltage control switch may be included between the power supply unit 122 and the current module 121, and the relay switch or semiconductor type voltage control switch may be turned on or off according to the control of the control unit 123. Through this, the control unit 123 may control to start, maintain, or stop the current supplied from the current module 121 to the light source 111.

The display unit 125 may display information such as a command according to a user manipulation, an operation of the control unit 123, and whether to drive the light source 111.

In general, it is used periodically more than a certain period of time when performing phototherapy. The control unit 123 may limit the irradiation time per one time to satisfy a condition less than the minimum erythema doses (MED) in a region of maximum irradiance touching the skin upon driving one time so as to prevent erythema.

In addition, even if the condition less than the MED is not satisfied, the control unit 123 may additionally limit a one-time ultraviolet rays exposure dose so as to prevent pigmentation or skin cancer that may occur during exposure to ultraviolet rays for a long time.

The control unit 123 may limit the light irradiation time during one-time driving of the light source 111 to prevent side effects due to overexposure to ultraviolet rays. The control unit 123 may drive the light source 111 for a preset period of time. After the light irradiation of the light source 111 starts, the control unit 123 may automatically stop the light irradiation of the light source 111 when the preset period of time elapses. According to an example, the control unit 123 may set a preset timer, for example, 10 minutes, from the time when turning on the relay switch for controlling the current supply of the current module 121, and when the timer expires, may turn off the relay switch. By doing this, the control unit 123 may limit the one-time irradiation time of the light source 111 to a predetermined time.

After the light irradiation of the light source 111 starts, the control unit 123 may stop the light irradiation when the preset period of time elapses. For example, the control unit 123 may drive the preset timer from the time when power required for driving is output to the light source 111, and when the timer expires, end output of the power required for driving to the light source 111.

The control unit 123 may drive the light source 111 in about 1 minute when the maximum irradiance reaching the skin per one time is 0.4 mW/cm$^2$ when performing phototherapy. The irradiance may be measured using the ultraviolet light sensor (112c in FIGS. 2 and 3), such as an ultraviolet sensitive photodiode, on a surface to which light is irradiated. The irradiance may be measured when the wearable illumination device 110 is manufactured.

Alternatively, after the ultraviolet light sensor (112c in FIGS. 2 and 3) is placed inside the wearable illumination device 110, the control unit 123 may calibrate relationship between the irradiance of an irradiation surface and an output value of the optical sensor 112c located inside to monitor whether the maximum allowable irradiance is exceeded. When the maximum allowable irradiance is exceeded, the control unit 123 may reduce the power output provided to the light source 111 in real time to operate within the maximum allowable irradiance.

The phototherapy of the wearable illumination device 110 may be irradiated to the same body part after at least one day has elapsed in order to prevent side effects such as skin erythema. At this time, the total amount of light may be adjusted not only through time but also through an area of light irradiation, and when the area of light irradiation is increased, the time of light irradiation for synthesizing the same amount of Vitamin D may be shortened, and may be effective in preventing side effects such as erythema formation. An effective area of light irradiation of the wearable illumination device 110 may be equal to or greater than 50 cm$^2$. A therapist may irradiate the plurality of wearable illumination devices 110 to different parts of the body in order to see the effect of increasing the area of light irradiation, or irradiate the same device to different parts of the body with a time difference.

The control unit 123 may adjust the total amount of light by adjusting a current supply time of the current module 121.

The control unit 123 may adjust the area of light irradiation by selectively driving the number of light sources to which current is supplied and/or positions of the light sources among the light sources 111 connected to the current module 121.

The memory 126 may store identification information of a device user and a usage record for each device user.

The alarm unit 127 may output an audible alarm to the outside. For example, the alarm unit 127 may output a voice message output, a ringtone, etc.

A driving control operation of the wearable illumination device 110 of the control unit 123 will be described for each embodiment as follows.

Figure 13:
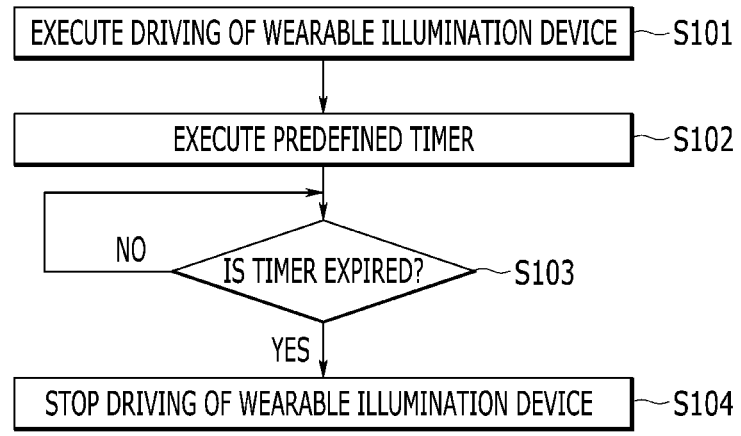
FIG. 13 is a flowchart illustrating a driving control operation of a wearable illumination device according to an embodiment.

FIG. 13 is a flowchart illustrating a driving control operation of a wearable illumination device according to an embodiment.

Referring to FIG. 13, the control unit 123 executes driving of the wearable illumination device 110 (S101). That is, in S101, the control unit 123 may instruct the current module 121 to supply current to the wearable illumination device 110.

The control unit 123 executes a predefined timer (S102), checks whether the predefined timer has expired (S103), and when the predefined timer expires, stops driving the wearable illumination device 110 (S104). That is, in S104, the control unit 123 may instruct the current module 121 to stop supplying the current to the wearable illumination device 110.

Figure 14:
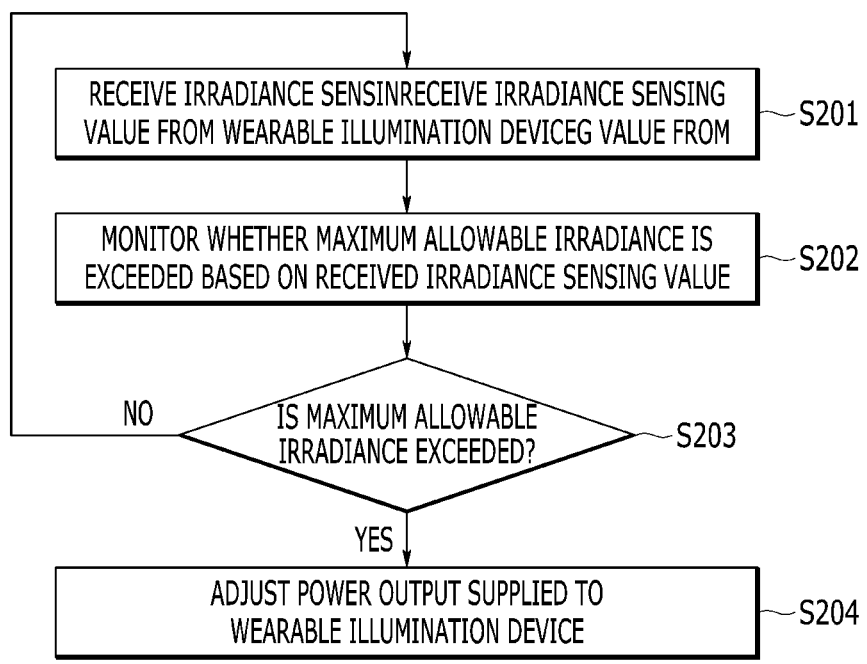
FIG. 14 is a flowchart illustrating a driving control operation of a wearable illumination device according to another embodiment.

FIG. 14 is a flowchart illustrating a driving control operation of a wearable illumination device according to another embodiment.

Referring to FIG. 14, the control unit 123 receives an irradiance sensing value from the optical sensor 112c of the wearable illumination device 110 (S201). In S201, the control unit 123 may be connected to the optical sensor 112c by wired or wirelessly to receive the irradiance sensing value.

The control unit 123 monitors whether a maximum allowable irradiance is exceeded based on the irradiance sensing value received in S201 (S202).

Based on a monitoring result of S202, the control unit 123 determines whether the irradiance sensing value received in S201 exceeds the maximum allowable irradiance (S203).

If the irradiance sensing value does not exceed the maximum allowable irradiance in S203, the control unit 123 performs again operations from S201.

When the irradiance sensing value exceeds the maximum allowable irradiance in S203, the control unit 123 adjusts a power output supplied to the wearable illumination device 110 (S204). For example, the control unit 123 may adjust an amount of current output, a current output time, the number of light sources to which current is supplied, positions of the light sources, etc.

Figure 15:
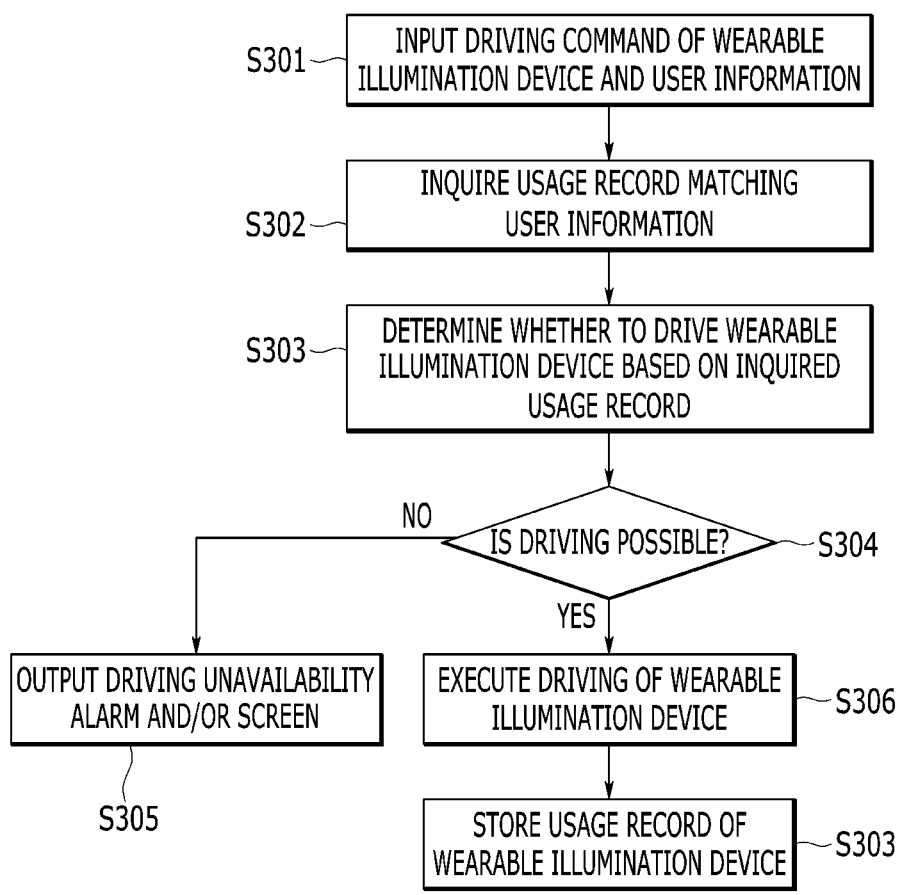
FIG. 15 is a flowchart illustrating a driving control operation of a wearable illumination device according to another embodiment.

FIG. 15 is a flowchart illustrating a driving control operation of a wearable illumination device according to another embodiment.

Referring to FIG. 15, the control unit 123 receives a driving command and user identification information of the wearable illumination device 110 from the user manipulation unit 124 (S301).

The control unit 123 inquires from the memory 126 a usage record matching the user identification information received in S301 (S302). At this time, the memory 126 is illustrated as an internal memory, but an external memory may be used. For example, the external memory may be included in a server computer, and the control unit 123 may be connected to the server computer through wired/wireless communication.

The control unit 123 determines whether to drive the wearable illumination device 110 based on the previous usage record inquired in S302 (S303). For example, a usage time of the wearable illumination device 110 may be limited to after 24 hours. Therefore, based on the previous usage record inquired in S302, when a determined time period, for example, 24 hours, has not elapsed since a last usage time of a specific user, the control unit 123 may limit the number of usages per day, by not allowing the driving of the wearable illumination device 110.

The control unit 123 determines whether driving is possible based on the determination of S303 (S304). When it is determined that driving of the wearable illumination device 110 is not allowed, the control unit 123 may request the alarm unit 127 to output a driving unavailability alarm or request the display unit 125 to output a driving unavailability message (S305).

When it is determined that driving of the wearable illumination device 110 is allowed, the control unit 123 may execute driving of the wearable illumination device 110 (S306) and store the usage record (S307). In S307, the control unit 123 may store the user identification information and the driving start time received in S301, and then when the use of the wearable illumination device 110 ends, record an end time in the memory 126.

The embodiment of the present disclosure described above is not implemented only through the device and the method, and may be implemented through a program realizing a function corresponding to the configuration of the embodiment of the present disclosure or a recording medium on which the program is recorded.

Although the embodiment of the present disclosure has been described in detail above, the scope of the present disclosure is not limited thereto, and various modifications and improvement forms of those skilled in the art using the basic concept of the present disclosure as defined in the following claims are also within the scope of the present disclosure.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

What is claimed is:

1. A wearable illumination device comprising:
   a housing formed in a structure that is wearable on a body,
   a light source installed in an inner part of the housing to radiate an ultraviolet light for inducing Vitamin D in the body to a skin of the body accommodated in the housing; and
   a light diffusion panel located between the light source and the skin, and configured to equalize an irradiance of the ultraviolet light reaching the skin by causing diffusion of the ultraviolet light radiated from the light source; and
   wherein in the light diffusion panel, a three-dimensional (3D) pattern that causes a light diffusion on an interface where the ultraviolet light is incident from the light source is formed, and
   wherein the 3D pattern comprises a micro-pattern of an inwardly concave shape toward the light diffusion panel on the interface, and a concave portion of the inwardly concave shape is toward an air gap formed between the housing and the light diffusion panel.

2. The wearable illumination device of claim 1, wherein:
   the light diffusion panel comprises light scattering particles having refractive indexes different from that of the light diffusion panel and causing the light diffusion of the ultraviolet light.

3. The wearable illumination device of claim 1, wherein: the light diffusion panel is made of a material having an ultraviolet ray transmittance equal to or greater than that of a polydimethylsiloxane (PDMS) material.

4. The wearable illumination device of claim 1, further comprising:
at least one spacer located between the housing and the light diffusion panel to separate the light source from the skin by a predetermined distance.

5. The wearable illumination device of claim 4, wherein: the at least one spacer has one side connected to the housing and the other side connected to the light diffusion panel and is formed at a height by which the light source is separated from the skin by the predetermined distance.

6. The wearable illumination device of claim 1, wherein: the housing is made of a flexible material so as to wrap an arm or leg of the body, has at least one hook-and-loop fastener attached to a fastening unit formed on one side and a fastening unit formed on the other side fastened to the at least one hook-and-loop fastener to fix the at least one hook-and-loop fastener, and is configured in a structure that wraps around the arm or the leg and is detachably worn on the arm or the leg.

7. The wearable illumination device of claim 1, wherein: the housing is integrally formed or assembled with a light blocking unit for shielding the ultraviolet light to prevent the ultraviolet light from leaking to an outside.

8. The wearable illumination device of claim 1, wherein: the light source comprises a plurality of light emitting diode (LED) devices,
the plurality of LED devices is connected to an electrode wiring on a flexible printed circuit board (FPCB) on which the electrode wiring is installed and are arranged in series or in parallel,
a connector to which a control device supplying a current to the plurality of light sources is connected to the electrode wiring, and
a heat sink for minimizing a heat transfer to the skin is installed at a point near a point where the plurality of light sources are installed in a rear surface of the FPCB.

9. A system for inducing synthesis of Vitamin D in a body, the system comprising:
a wearable illumination device comprising a housing formed in a structure that is wearable on the body, and a plurality of light sources configured to radiate an ultraviolet light to a skin of a worn part; and
a microcontroller unit (MCU) configured to drive the plurality of light sources to radiate the ultraviolet light,
wherein the wearable illumination device further comprises
a light diffusion panel configured to equalize an irradiance of the ultraviolet light reaching the skin by causing diffusion of the ultraviolet light radiated from the plurality of light sources,
wherein in the light diffusion panel, a three-dimensional (3D) pattern that causes a light diffusion on an interface where the ultraviolet light is incident from the plurality of light sources is formed, and
wherein the 3D pattern comprises a micro-pattern of an inwardly concave shape toward the light diffusion panel on the interface, and a concave portion of the inwardly concave shape is toward an air gap formed between the housing and the light diffusion panel.

10. The system of claim 9, wherein the MCU is configured to, after starting to supply a current to the plurality of light sources, when a preset time elapses, stop supplying the current.

11. The system of claim 10, wherein:
the wearable illumination device comprises an optical sensor configured to measure an irradiance of the ultraviolet light radiated to the skin, and
wherein the MCU is configured to receive an irradiance measurement value of the ultraviolet light from the optical sensor, when the irradiance measurement value exceeds a set maximum irradiance, adjust at least one of a current output amount, a current output time, a number of light sources to which the current is supplied, and positions of the light sources, and reduce the irradiance of the ultraviolet light radiated to the skin.

12. The system of claim 11, wherein the MCU is further configured to limit an irradiation time per one time to satisfy a condition less minimum erythema doses in a region of maximum irradiance touching the skin upon driving one time.

13. The system of claim 9, wherein: the control device comprises
the microcontroller unit (MCU) configured to check a last usage time by inquiring a previous usage record matching identification information received from a user, and determine whether to drive the wearable illumination device based on whether a determined time period has elapsed from the last usage time,
wherein the MCU is configured to, when it is determined to drive the wearable illumination device, match a usage record with the identification information of the user and store the usage record including a driving start time and a driving end time.

\* \* \* \* \*